US006506473B1

(12) United States Patent
Hisanaka et al.

(10) Patent No.: US 6,506,473 B1
(45) Date of Patent: *Jan. 14, 2003

(54) COMPOSITE PLASTIC SHEET AND PROCESS FOR MAKING THE SAME

(75) Inventors: Takayuki Hisanaka, Kagawa-ken (JP); Hisashi Takai, Kagawa-ken (JP); Koichi Yamaki, Kagawa-ken (JP)

(73) Assignee: Uni-Charm Corporation, Ehime-ken (JP)

(*) Notice: Subject to any disclaimer, the term of this patent is extended or adjusted under 35 U.S.C. 154(b) by 153 days.

This patent is subject to a terminal disclaimer.

(21) Appl. No.: 09/606,941

(22) Filed: Jun. 29, 2000

(30) Foreign Application Priority Data

Jun. 29, 1999 (JP) .......................................... 11-184428

(51) Int. Cl.[7] .............................................. A61F 13/15
(52) U.S. Cl. ...................... 428/138; 428/131; 428/133; 428/137; 604/358; 604/365; 604/378; 604/383; 604/385.01; 604/385.101
(58) Field of Search ................................. 604/358, 365, 604/366, 378, 383, 385.01, 385.08, 385.101, 385.31; 442/327; 428/131, 133, 137, 138

(56) References Cited

U.S. PATENT DOCUMENTS

| 3,731,688 A | * | 5/1973 | Litt et al. ..................... 604/364 |
| 4,282,874 A | * | 8/1981 | Mesek ......................... 128/287 |
| 4,614,679 A | * | 9/1986 | Farrington et al. ............. 15/215 |
| 4,988,344 A | * | 1/1991 | Reising et al. ................. 604/358 |
| 6,117,524 A | * | 9/2000 | Hisanaka et al. .............. 428/131 |

FOREIGN PATENT DOCUMENTS

EP 0 919 212 A 6/1999

OTHER PUBLICATIONS

Copy of European Search Report, EP 00 30 5452, dated Sep. 22, 2000.

* cited by examiner

Primary Examiner—Harold Pyon
Assistant Examiner—Alicia Chevalier
(74) Attorney, Agent, or Firm—Baker & Daniels

(57) ABSTRACT

A topsheet for a disposable absorbent article that includes a first hydrophobic plastic film layer, a second hydrophobic plastic film layer and hydrophobic thermoplastic synthetic fibrous layer disposed between the two layers. The first hydrophobic plastic film layer includes a plurality of first plane regions spaced apart from one another that extend parallel to one another in one direction and the second hydrophobic plastic first layer includes a plurality of second plane regions spaced apart from one another that extend parallel to one another in the one direction. Of the first and second plane regions, at least the first plane regions are formed with bridge regions and first rising regions.

6 Claims, 13 Drawing Sheets

COMPOSITE PLASTIC SHEET AND PROCESS FOR MAKING THE SAME

BACKGROUND OF THE INVENTION

This invention relates to a composite sheet suitable as a component of disposable garments such as disposable diapers, sanitary napkins and disposable gowns used in medical fields and also to a process for making such a composite sheet.

It is well known to use a plastic film or nonwoven fabric as breathable but liquid-resistant sheet constituting disposable garments. As it is well known, a hydrophobic plastic film may be added with grains of inorganic filler such as barium sulfate and then stretched to obtain a liquid-resistant plastic film having fine pores for breathability. As it is also well known, hydrophobic thermoplastic synthetic fiber may be processed to form a nonwoven fabric having an appropriately high fiber density, i.e. appropriately small fiber interstices and thereby presenting desired breathability and liquid-resistance. It is also possible to improve the liquid-resistance by subjecting the nonwoven fabric to water repellent finish.

The term "liquid-resistance" used herein should be understood to mean a property enabling permeation as well as exudation of body fluids to be practically avoided.

The plastic film of prior art may give a wearer of the disposable garment using such plastic film so-called plastic-like touch peculiar to such plastic film and the plastic-like touch is often disliked by the wearer. On the contrary, the nonwoven fabric rarely gives the wearer a plastic-like touch even when the nonwoven fabric is made of raw material similar to that of the plastic film. Increasing of the fiber density certainly results in an improvement of the liquid-resistance but at the cost of a soft touch desired for the nonwoven fabric, an increased amount of the fiber used to make the nonwoven fabric and a correspondingly higher cost of the nonwoven fabric are realized.

SUMMARY OF THE INVENTION

It is an object of this invention to provide a breathable but liquid-resistant composite sheet offering a soft and comfortable touch.

According to a first aspect of this invention, there is provided a composite plastic sheet suitable a component of disposable garment and, according to second-fourth aspects of this invention, there is provided a process for making the composite sheet.

The first aspect of this invention relates to a composite plastic sheet comprising a first plastic film layer forming an upper surface of the sheet, a second plastic film layer forming a lower surface of the sheet and a thermoplastic synthetic fibrous assembly layer disposed between the first and second plastic film layers and joined to the first and second plastic film layers, respectively.

According to the first aspect of this invention, the first and second plastic film layers and the fibrous assembly layer are hydrophobic; the first plastic film layer includes a plurality of first plane regions spaced one from another and extending parallel one to another in one direction and the second plastic film layer includes a plurality of second plane regions spaced one from another and extending parallel one to another in the one direction wherein each of the first and second plane regions has a thickness of 0.001~0.05 mm and a width of 0.03~1 mm and wherein, of each pair of adjacent the first plane regions and each pair of adjacent the second plane regions, at least each pair of adjacent the first plane regions are connected with each other by a plurality of bridge-like regions extending across the adjacent plane regions; of the first and second plane regions, at least first plane regions are formed along edges thereof with first rising regions extending upward from an upper surface of the plane regions so as to undulate sawtooth waves in the one direction;

the second plastic film layer partially underlies regions of the fibrous assembly layer defined between each pair of adjacent the first plane regions; and the fibrous assembly layer comprises component fibers joined together by mechanical entanglement, heat-sealing or adhesion joined and is joined to a lower surface of the first plane regions and an upper surface of the second plane regions.

The second aspect of this invention relating to a process for making a composite plastic sheet comprises the steps of:

a. continuously feeding a composite web comprising a hydrophobic plastic film web and a thermoplastic synthetic fibrous assembly web underlying the film web and joined to a lower surface of the film web in one direction;

b. subjecting a lower surface of the continuously fed composite web to high pressure columnar water streams and thereby breaking through the film web the high pressure columnar water streams in the one direction according to traces of the high pressure columnar water streams to form the film web with a plurality of first plane regions extending parallel one to another in the one direction, a plurality of openings extending parallel one to another in the one direction between respective pairs of adjacent the first plane regions, a plurality of first rising regions extending from edges of the first plane regions defining respective the openings substantially in the same direction as the high pressure columnar water streams so as to undulate in the one direction substantially like sawtooth waves, and a plurality of bridge-like regions extending across respective the openings to connect each pair of adjacent the plane regions with each other; and c. joining a plurality of plastic film strips extending parallel one to another in the one direction to a lower surface of the fibrous assembly so that the plastic film strips at least partially underlie portions of the fibrous assembly web defined by respective the openings.

The third aspect of this invention relating also to a process for making a composite plastic sheet comprises the steps of:

a. continuously feeding composite web comprising a plastic film web and a fibrous assembly web underlying the film web and joined to a lower surface of the film web in one direction;

b. subjecting an upper surface of the continuously fed composite web to high pressure columnar water streams and thereby breaking through the film web by the high pressure columnar water streams in the one direction according to traces of the high pressure columnar water streams;

c. subjecting a lower surface of the composite web, substantially in accordance with the traces of the high pressure columnar water streams, to high pressure columnar water streams to form the film web with a plurality of first plane regions extending parallel one to another in the one direction, a plurality of openings extending parallel one to another in the one direction between respective pairs of adjacent the first plane regions, a plurality of first rising regions extending from edges of the first plane regions defining respective the openings substantially in the same direction as the high pressure columnar water streams so as to undulate in the one direction substantially like sawtooth waves, and a plurality of bridge-like regions extending across respective the openings to connect each pair of adjacent the plane regions with each other; and d. joining a plurality of plastic film strips extending parallel one to another in the one direction to a lower surface of the fibrous assembly web so that the plastic film strips at least partially underlie portions of the fibrous assembly defined by respective the openings.

The fourth aspect of this invention relating also to a process formaking a composite plastic sheet comprises the steps of:

a. continuously feeding composite web in one direction, the composite web comprising an upper plastic film web, a lower plastic film web and a fibrous assembly web disposed between the upper plastic film web and joined to a lower surface of the upper plastic film web and to an upper surface of the lower plastic film web in one direction; and b. subjecting an upper surface of the continuously fed composite web to high pressure columnar water streams and thereby breaking through the upper and lower plastic film web in according with traces of the high pressure columnar water streams in the one direction to form the upper and lower plastic film with a plurality of first plane regions extending parallel one to another in the one direction, a plurality of openings extending parallel one to another in the one direction between respective pairs of adjacent the first plane regions, a plurality of first rising regions extending from edges of the first plane regions defining respective the openings substantially in the same direction as the high pressure columnar water streams so as to undulate in the one direction substantially like sawtooth waves, and a plurality of bridge-like regions extending across respective the openings to connect each pair of adjacent the plane regions with each other.

DETAILED DESCRIPTION OF THE PREFERRED EMBODIMENTS

Details of a composite plastic sheet according to this invention and a process for making the same will be more fully understood from the description given here under with reference to the accompanying drawings.

Figure 1:
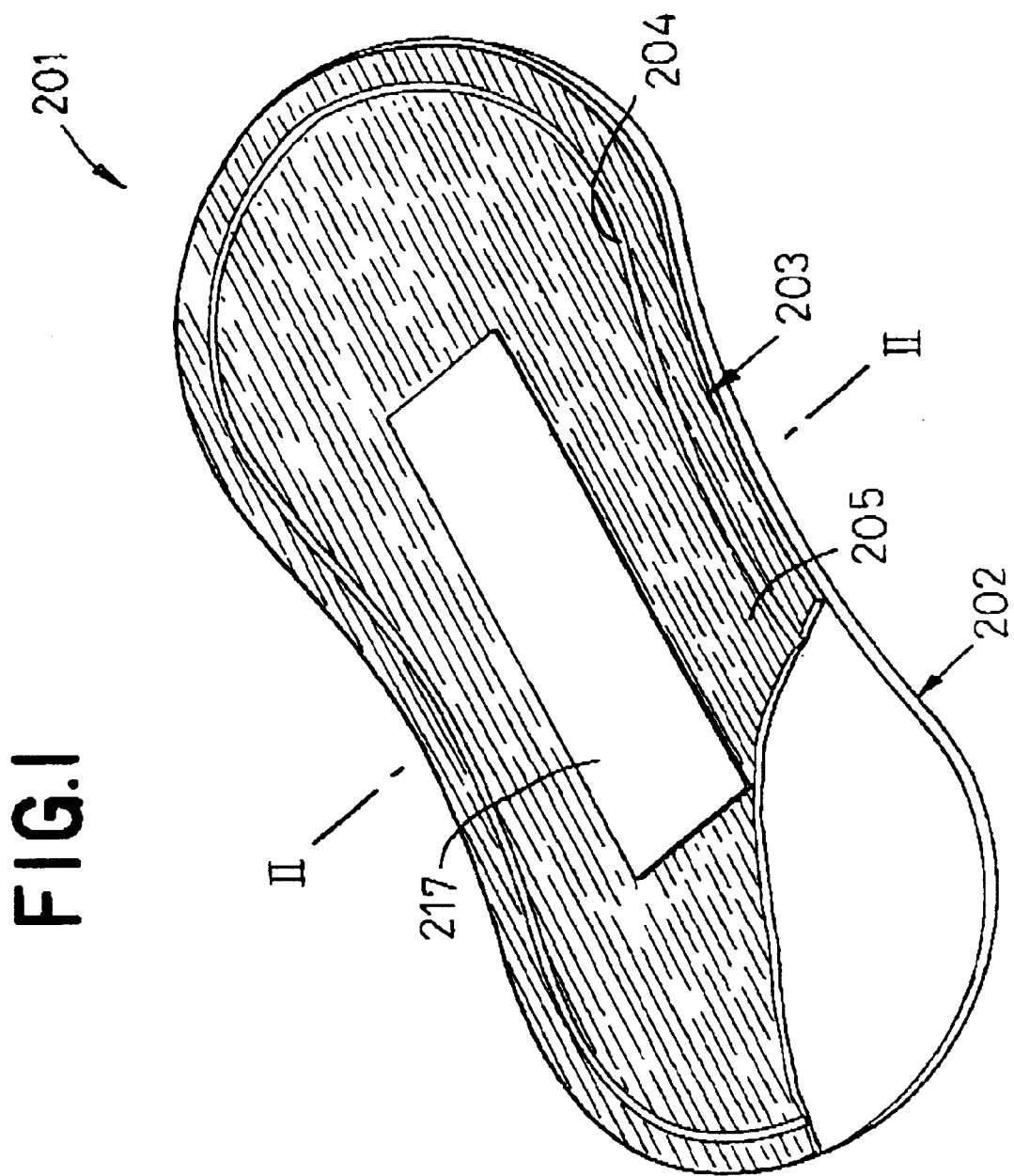
FIG. 1 is a perspective view showing a panty liner partially broken away.
Figure 2:
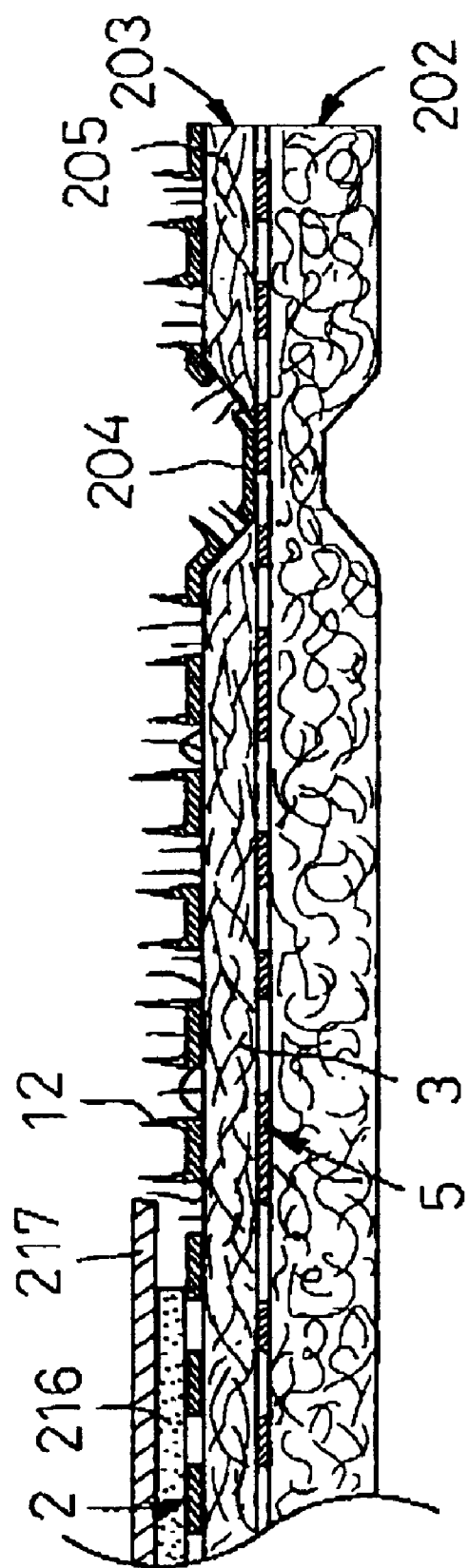
FIG. 2 is a sectional view taken along line II—II in FIG. 1.

FIG. 1 is a partially cutaway perspective view showing a panty liner 201 as a specific example of disposable garments with its lower side up and FIG. 2 is a sectional view taken along line II—II in FIG. 1. The panty liner 201 comprises a body fluid absorbent layer 202 intended to come in contact with the wearer's skin and a liquid-resistant layer 203 intended to be placed against the wearer's shorts. These two layers 202, 203 are mechanically engaged together along an embossing line 204 extending along a peripheral edge of the liner 201.

The body fluid absorbent layer 202 is provided in the form of a water-absorbent sheet-like layer comprising water-absorbent fiber such as fluff pulp or rayon fiber or a mixture of such water-absorbent fiber and highly water-absorbent polymer or the like. The layer 202 is suitable for absorption of a small amount of menstrual discharge or other body fluids.

The liquid-resistant layer 203 is formed by the composite plastic sheet 205 according to this invention. The sheet 205 comprises a hydrophobic inner plastic film layer 5 placed upon the absorbent layer 202, a hydrophobic outer plastic film layer 2 intended to come in contact with a garment put on the wearer's body, and a hydrophobic intermediate fibrous assembly layer 3 disposed between the layers 2, 5. The outer plastic film layer 2 includes an adhesive region 216 functioning a fastening means by means of which the outer plastic film layer 2 is fastened to the garment of the wearer. The adhesive region 216 is protectively covered with a strip of release paper 217 before the liner 201 is actually used. The liquid-resistant layer 203 functions to prevent body fluids from permeating through the absorbent layer 202 to the shorts of the wearer and the presence of the liquid-resistant layer 203 thus protects the garment of the wearer from being soiled with body fluids.

Figure 3:
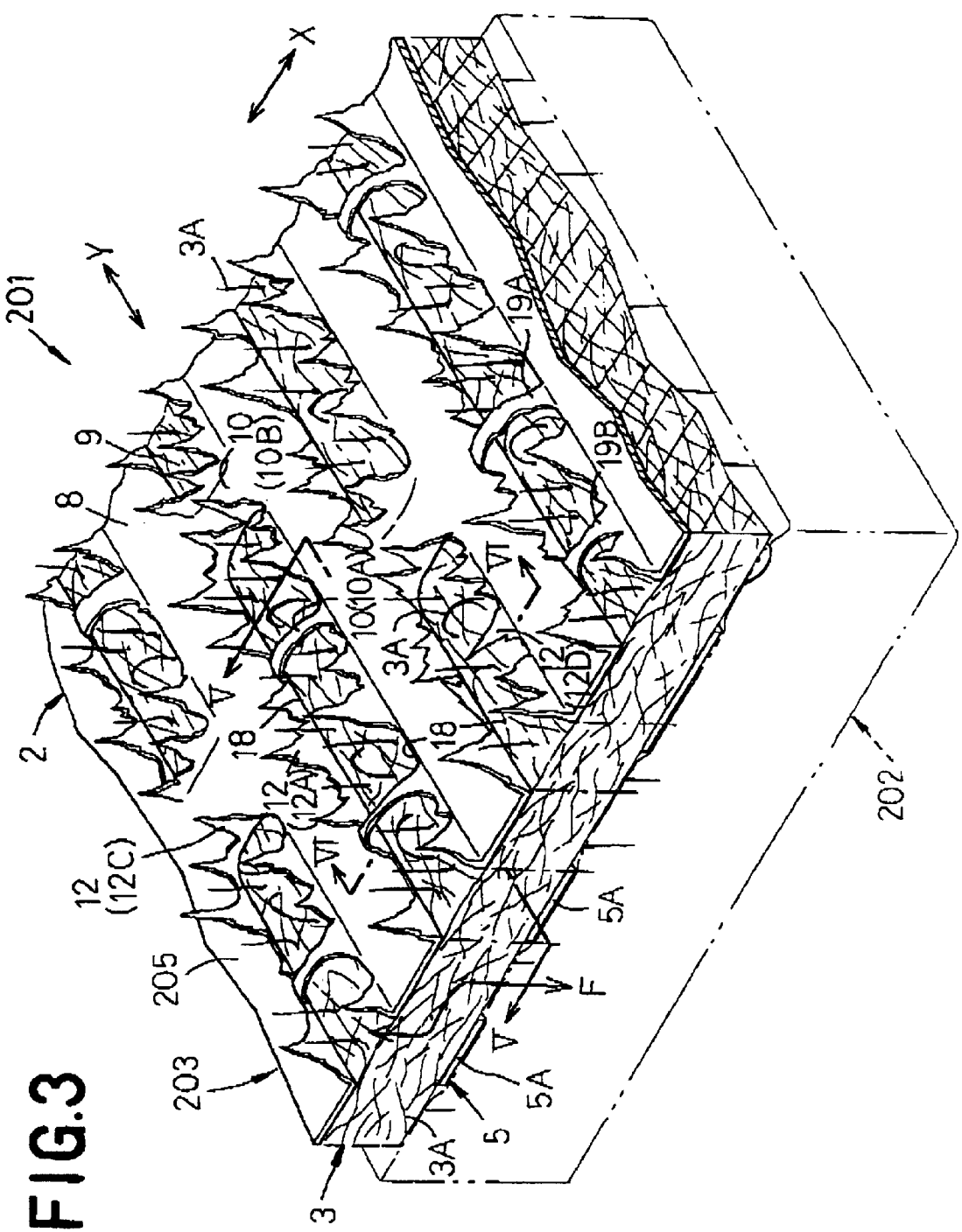
FIG. 3 is a fragmentary perspective view of a composite sheet.
Figure 4:
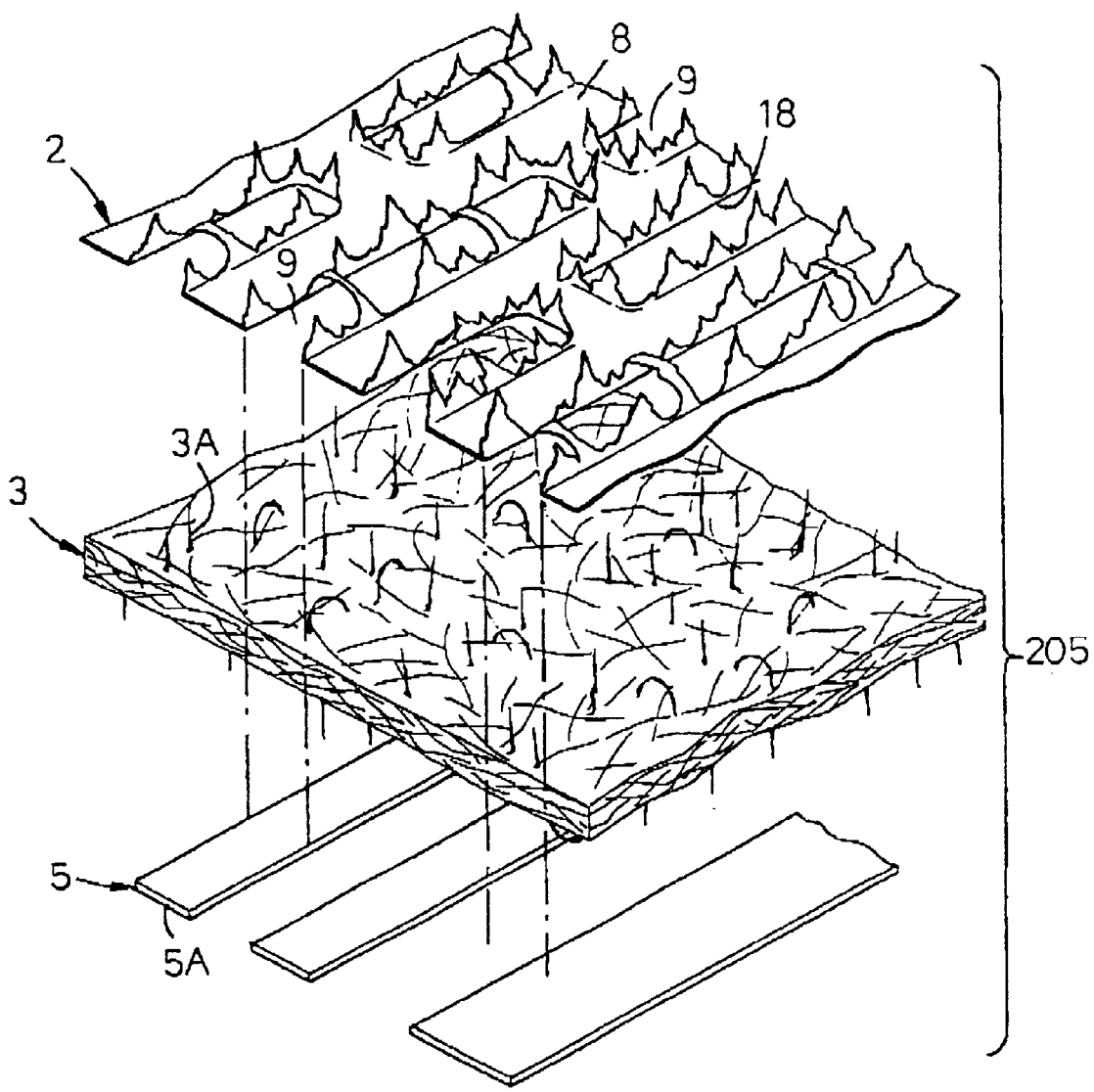
FIG. 4 is an exploded perspective view of the composite sheet.

FIG. 3 is a fragmentary perspective view of the composite sheet 205 constituting the liquid-resistant layer 203 and FIG. 4 is a perspective view showing component members of the composite sheet 205 as being exploded in the vertical direction.

The outer plastic film layer 2 making a part of the liquid-resistant layer 203 is of a flexible nature and comprises a plurality of substantially plane regions 8 extending parallel one to another in a direction indicated by a double-headed arrow Y, a plurality of openings 9 extending in the direction Y between each pair of adjacent plane regions 8, bridge-like regions 10 extending across each of the openings 9 in a direction indicated by a double-headed arrow x to connect opposite edges 18 of each of said openings, and rising regions 12 extending upward, as viewed in FIG. 2, from the edges 18 of the plane regions 8. Said rising regions 12 irregularly undulate in the direction Y to form sawtooth waves.

The fibrous assembly layer 3 is flexible and joined to the plane regions 8 of the outer plastic film layer 2 from below as viewed in FIG. 2 so that the assembly layer 3 may be partially exposed within the respective openings 9. Within the openings 9, component fibers 3A of the assembly layer 3 partially extend outwardly of the composite sheet 20, i.e., upward as viewed in FIG. 2, linearly or so as to describe circular arcs.

The inner plastic film layer 5 comprises a plurality of plane film strips 5A extending parallel one to another in the direction Y and joined to the fibrous assembly layer 3 from below as viewed in FIG. 2. In this manner, the inner plastic film layer 5 forms at least a part of the lower surface of the liquid-resistant layer 203. The fibrous assembly layer 3 is partially exposed between each pair of adjacent film strips 5A, 5A and, in these exposed regions, the component fibers 3A of the assembly layer 3 partially extend toward the absorbent layer 202 so as to describe straight lines or circular arcs.

Referring to FIGS. 3 and 4, single dot chain lines extending downward from the edges 18 of the outer plastic film layer 2 function to project the respective openings 9 upon the lower surface of the fibrous assembly layer 3. Each of the film strips 5A partially underlies each region of the fibrous assembly layer 3 defined by each of the openings 9.

Figure 5:
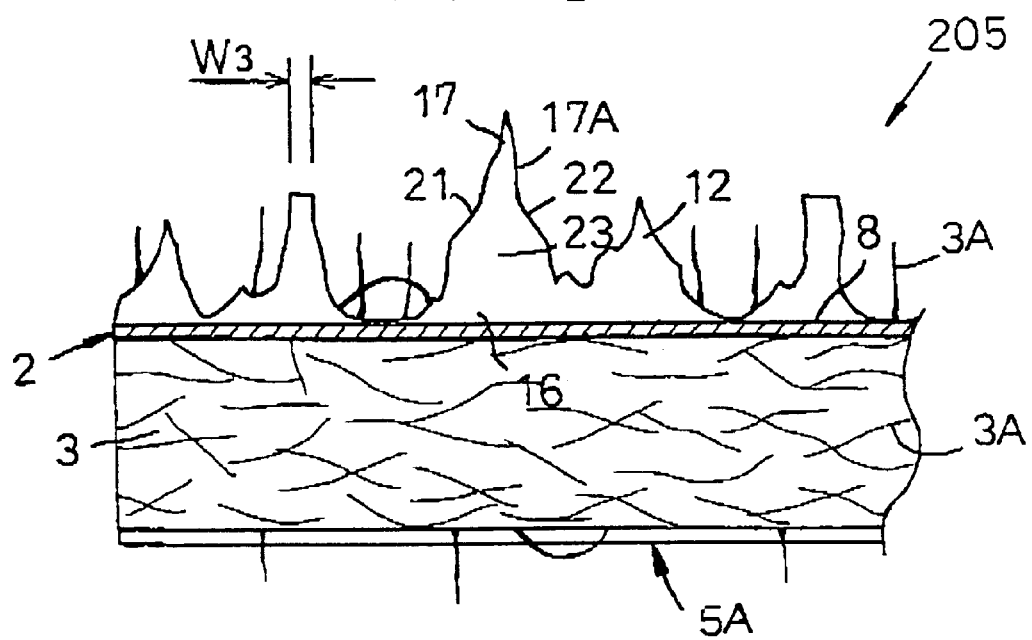
FIG. 5 is a sectional view taken along line V—V in FIG. 3.
Figure 6:
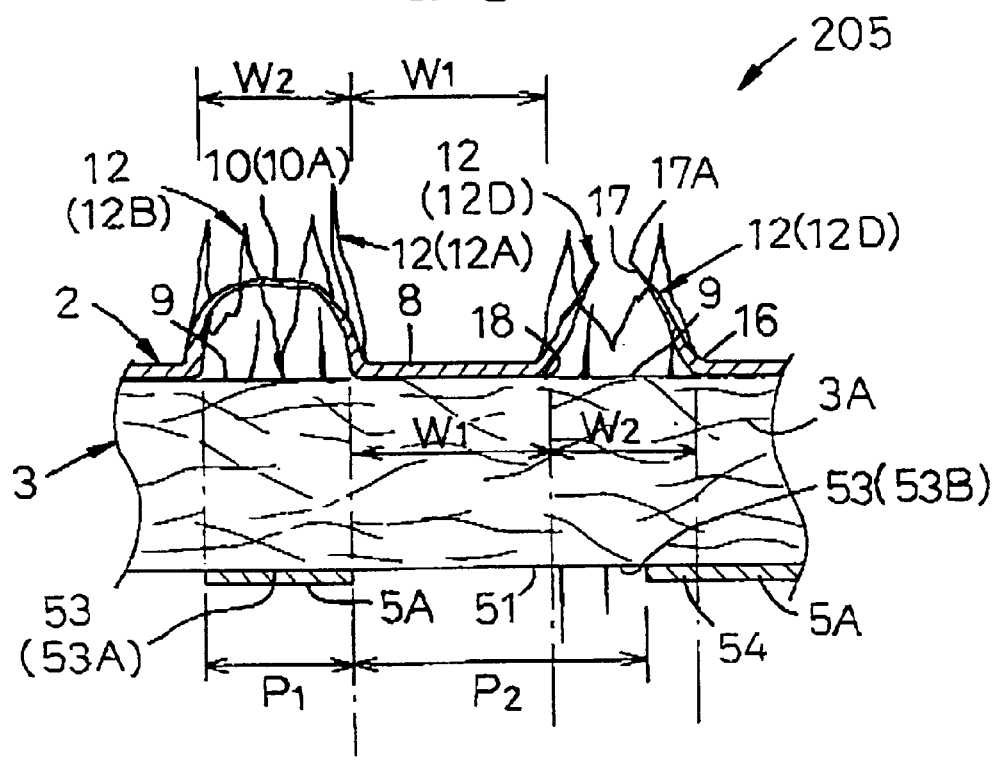
FIG. 6 is a sectional view taken along line VI—VI in FIG. 3.

FIGS. 5 and 6 are sectional views respectively taken along lines V—V and VI—VI.

Referring to FIGS. 5 and 6, the outer plastic film layer 2 is made of hydrophobic thermoplastic material, of which the flat regions 8 have a thickness of 0.001~0.05 mm and a width $W_1$ of 0.03–1 mm as measured in the direction X between each pair of adjacent openings 9, 9. Most of these openings 9 has a larger dimension in the direction Y. Each of the openings 9 preferably has a width $W_2$ of 0.05–1 mm and a length corresponding to 1.5 times of the width $W_2$ or larger.

The bridge-like regions 10 of the outer plastic film layer 2 are formed intermittently in the direction Y. The bridge-like regions 10 include plane bridge-like regions 10A which are flush with the plane regions 8 and arc-shaped bridge-like regions 10B which include, in turn, bridge-like regions 10B having their proximal ends 19A appearing to extend from the plane regions 8 and bridge-like regions 10B having their proximal ends 19B appearing to extend in continuity with the rising regions 12 (Reter also to FIG. 3). The bridge-like regions 10 preferably have a thickness equal to or less than the thickness of the plane regions 8 and a width $W_3$ in the direction Y (Refer to FIG. 5) of at least 0.001–2 mm.

A large majority of the rising regions 12 that are identified by reference numeral 12A are formed by a portion of the outer plastic film layer 2 extending upward as viewed in FIG. 3 from edges of the film layer 2. These rising regions 12A have proximal ends 16 contiguous to the respective plane regions 8 and free ends 17 extending upward from the proximal ends 16. The upper edges 17A of the respective free ends 17 undulate along the respective edges 18. A height of the upper edges 17A as measured from the plane regions 8 varies in a range of 0–1 mm. The rising regions 12 include those identified by reference numeral 12C which are formed along edges of the bridge-like regions 10 and have a substantially the same height as said rising regions 12A (Refer also to FIG. 3).

The embodiment in which the upper edges 17A of the rising regions 12A undulate to form sawtooth waves will be described more in details with reference to FIG. 5. The rising regions 12A comprise an irregular array of triangular or substantially triangular portions 23 each defined by a substantially rightward ascendant oblique side 21, a substantially leftward ascendant oblique side 22 and the proximal end 16 extending between these two oblique sides 21, 22. The rising regions 12C also may undulate in the similar manner to the rising regions 12A. The rising regions 12 comprising these rising regions 12A, 12C have a thickness equal to or less than the thickness of the plane regions 8 so that the rising regions 12 may be smoothly deformed as they come in contact with the wearer's skin and consequently the surface of the liquid-resistant layer 203 may smooth and soft touch to the wearer. While it will be difficult to visually recognize the individual rising regions 12, a plurality of rising regions 12 as a whole give the surface of the composite sheet 205 a fluffy appearance. The rising regions 12 diffusively reflect the light incident thereupon and thereby alleviate surface gloss peculiar to the plastic film.

The outer plastic film layer 2 including a plurality of openings 9 preferably has a breathability of 5~700 $cm^3$/$cm^2$·sec as measured according to the prescription of JIS (Japanese Industrial Standards)-L-1096 and a moisture resistance of 0–200 mm as measured according to the prescription of JIS-L-1092. The film layer 2 is made of material selected from a group consisting of a hydrophobic thermoplastic film and an originally hydrophobic thermoplastic film treated to become hydrophilic. The film used as stock material for the layer 2 may contain suitable colorant or filler such as titanic oxide or barium sulfate.

The fibrous assembly layer 3 is made of material selected from a group consisting of thermoplastic synthetic fiber, chemical fiber such as rayon fiber, a mixture of these synthetic fiber and chemical fiber, and such synthetic fiber and/or chemical fiber mixed with cotton fiber and/or pulp fiber. The fibrous assembly layer 3 contains hydrophilic fiber of 5 w/w % or higher, preferably of 10 w/w % or higher, more preferably of 20 w/w % or higher. More preferably, the assembly layer 3 comprises nonwoven fabric having a basis weight of 2~50 g/$m^2$, in which the component fibers are mechanically entangled and heat-sealed or adhesively joined together. The nonwoven fabric containing thermoplastic synthetic fiber or chemical fiber having a fineness of 0.05~15 deniers may be selected from a group consisting of a spun bond nonwoven fabric, a point bond nonwoven fabric, a thermal bond nonwoven fabric such as an air-through nonwoven fabric, a melt blown nonwoven fabric and a , spun lace nonwoven fabric. In its thickness direction, the fibrous assembly layer 3 preferably has a breathability of 5~700 $cm^3$/$cm^2$·sec as measure according to the prescription JIS–L–1096 and a moisture resistance of 0–200 mm as measured according to the prescription JIS–L–1092. Bonding the assembly layer 3 to the upper film layer 2 and to the lower film layer 5 may be carried out using heat-or supersonic-sealing or a suitable adhesive agent such as a hot melt adhesive agent.

Each of the film strips 5A constituting the inner plastic film layer 5 has a thickness of 0.001~0.05 mm, a width $P_1$ of 0.03~1.5 mm. Each pair of adjacent film strips 5A, 5A define therebetween a gap 51 (See FIG. 6) having a width $P_2$ of 0.03~2 mm, preferably of 0.03–1 mm. Similarly to each pair of adjacent plane regions 8 in the outer plastic film layer 2, each pair of adjacent film strips 5A may be also connected to each other via bridge-like regions extending across the gap 51 left between these adjacent film strips 5A. As imaginary lines indicate in FIG. 6, regions 53 corresponding to the openings 9 of the outer plastic film layer 2 projected upon the lower surface of the fibrous assembly layer 3 are partially occupied by the film strips 5A. For example, a particular one 53A of these regions 53 is occupied by the film strip 5A having a substantially the same width as the opening lying above this film strip 5A. Another particular region 53B is partially occupied by a side edge portion 54 of the film strip 5A lying immediately beneath the corresponding plane region 8. The film strips 5A may contain suitable colorant such as titanic oxide or barium sulfate.

In the panty liner 201, the composite sheet 205 constructed as has been described above is used to cover the lower surface (the upper surface as viewed in FIG. 3) of the body fluid absorbent layer 202 as indicated by two-dot-chain-lines. With such liner 201, air channels extending from the openings 9 to the gaps 51 defined between respective pairs of adjacent film strips 5A as indicated by two dot chain lines and these air channels allow the liner 201 to be breathable and free from stuffiness.

In the liner 201 after its used, the amount of absorbed menstrual discharge is substantially concealed from the wearer's eyes by the plane regions 8 and said film strips 5A, respectively, when the liner 201 is looked from its lower side. While the amount of menstrual discharge staying between each pair of adjacent plane regions 8, 8 otherwise might be seen through the openings 9, such amount of menstrual discharge is effectively concealed from the wearer's eyes by the rising regions 12 so far as the rising regions 12 take their positions leaning inwardly of the openings 9. Accordingly, in this liner 201, the liquid-resistant layer 203 ensures a high breathability and no significant amount of menstrual discharge is conspicuous through the liquid-resistant layer 203. The rising regions 12 leaning inwardly of the openings 9 are exemplarily illustrated in FIG. 6 as the rising regions 12D. In addition, the liquid-resistant layer 203 presents a velvet-like comfortable touch afforded by the thin and soft rising regions 12 of the outer plastic film layer 2.

Figure 7:
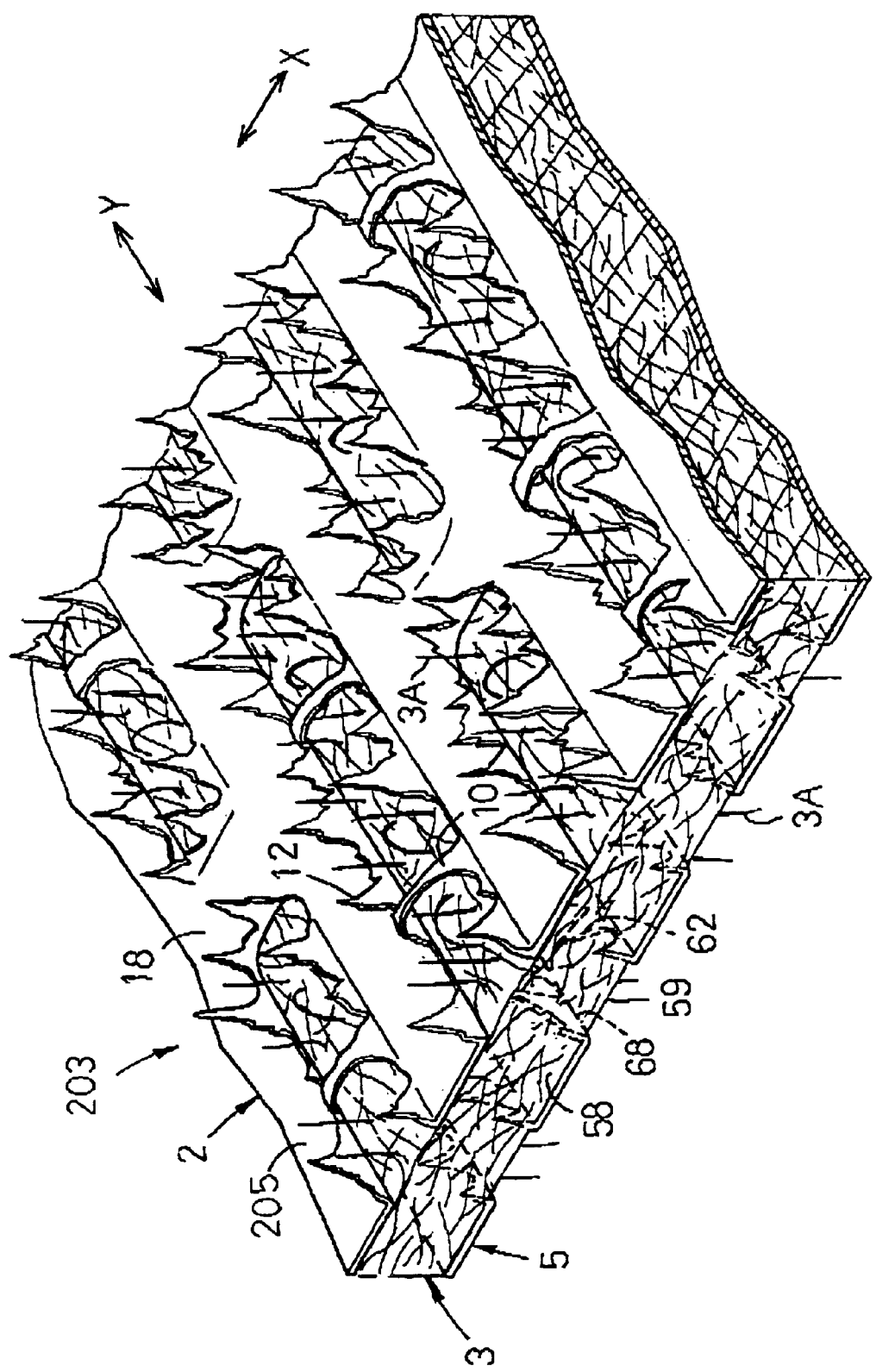
FIG. 7 is a view similar to FIG. 3 but showing another embodiment.
Figure 8:
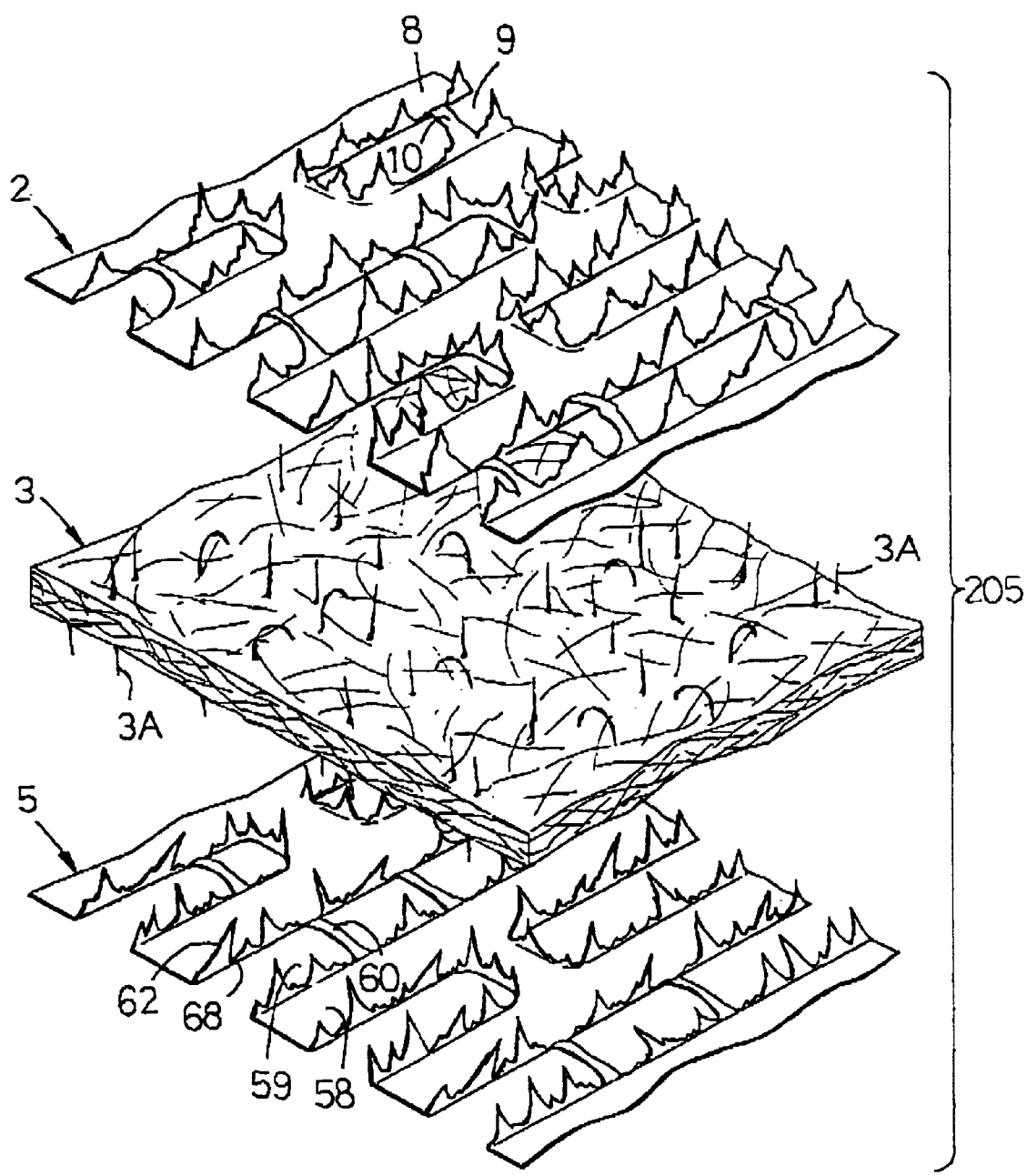
FIG. 8 is an exploded perspective view of the composite sheet shown by FIG. 7.

FIGS. 7 and 8 are perspective and exploded perspective views similar to FIGS. 3 and 4, respectively, but show another embodiment of this invention. Referring to FIG. 8, the outer plastic film layer 2, the intermediate fibrous assembly layer 3 and the inner plastic film layer 5 are illustrated to be separated one from another in the vertical direction. The outer plastic film layer 2 and the fibrous assembly layer 3 of these three layers are similar to the corresponding layers 2, 3 in FIG. 4. However, the inner plastic film layer 5 has a configuration which is not similar to that of the inner plastic film layer 5 but to that of the outer plastic film layer 2 of FIG. 4. Specifically, the inner plastic film layer 5 of FIGS. 7 and 8 comprises plane regions 58, openings 59, bridge-like regions 60 and rising regions 62 extending upward from the edges 68 of the respective plane regions 58. Within the respective openings 9, 59, the component fibers 3A of the fibrous assembly layer 3 extend upward or downward so as to describe straight lines or circular arcs.

In the composite sheet 205 comprising these outer plastic film layer 2, fibrous assembly layer 3 and inner plastic film layer 5 placed one upon another and joining together, the openings 9 of the outer plastic film layer 2 are aligned with the openings 59 of the inner plastic film layer 5 in the thickness direction of the sheet 205. In other words, the openings 9 respectively have their positions as well as their widths coinciding with the corresponding openings 59 as viewed in the direction X. However, this is not necessarily true for the relative position between the bridge-like regions 10, 60 associated with the openings 9, 59, respectively. The rising regions 62 of the inner film layer 5 comprise those vertically extending into the fibrous assembly layer 3 from the edges 68 of the respective plane regions 58 and those extending from the edges 68 to lean inwardly of the respective openings 59. The rising regions 62 are hydrophobic and not readily wettable with menstrual discharge and therefore prevent the amount of menstrual discharge from moving downward beyond a level of the rising regions 62 into the openings 59. The rising regions 62 extending to lean inwardly of the openings 59 are effective to intercept the amount of menstrual discharge absorbed by the absorbent layer 202 and thereby causing it to stay immediately above the respective openings 59 away from the wearer's eyes. The bridge-like regions 60 function in the similar manner.

Figure 9:
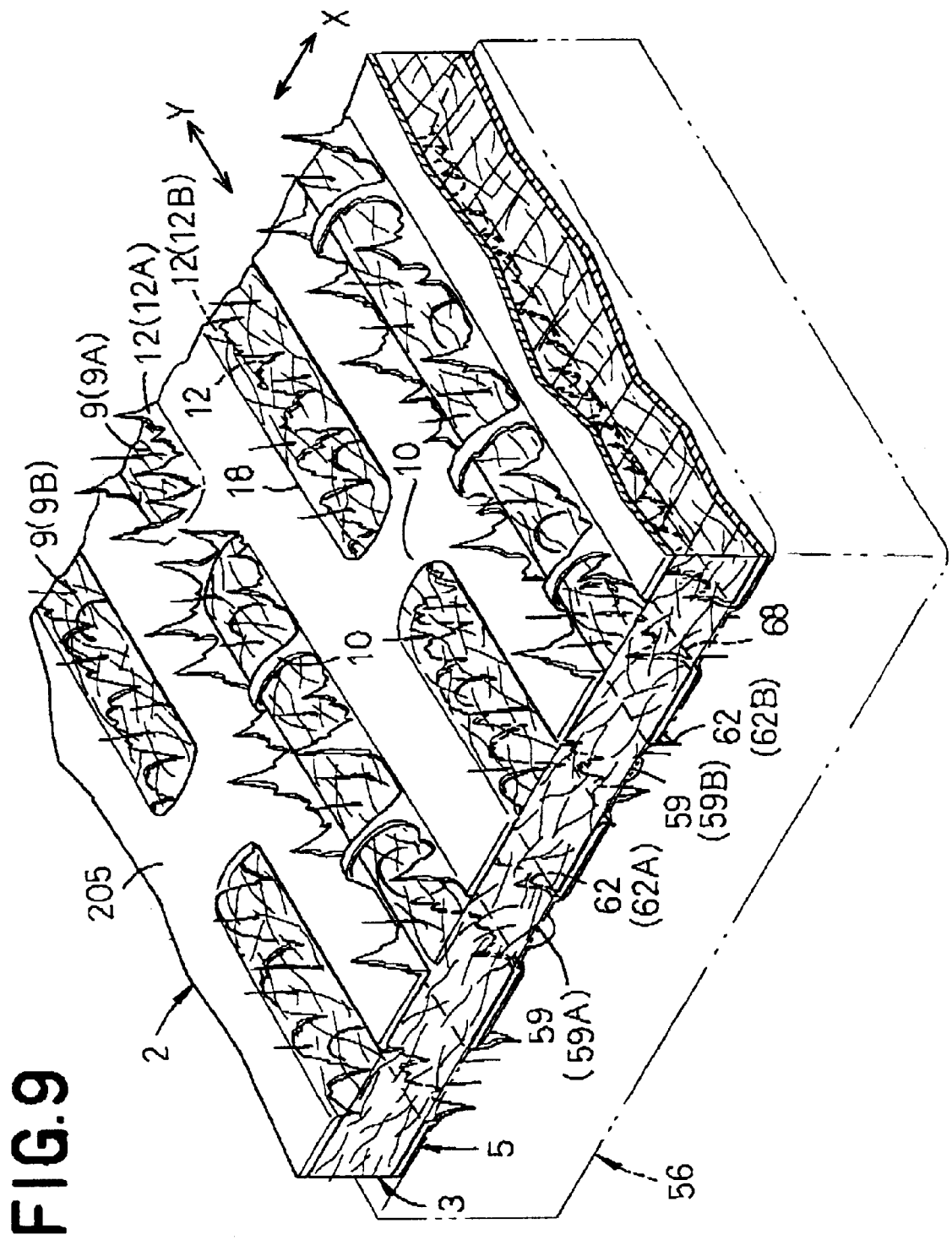
FIG. 9 is a view similar to FIG. 3 but showing still another embodiment.
Figure 10:
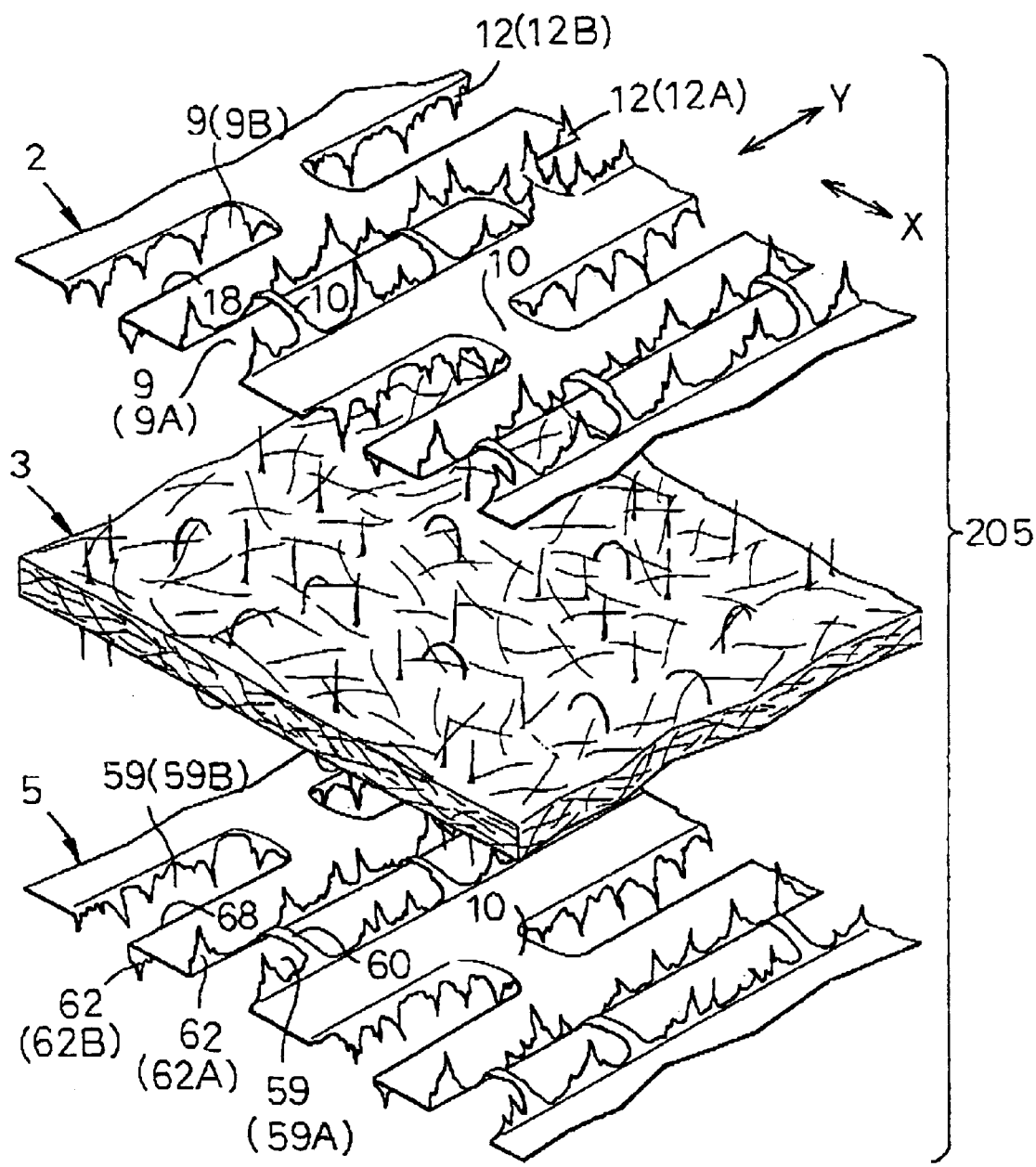
FIG. 10 is an exploded perspective view of the composite sheet shown by FIG. 9.

FIGS. 9 and 10 are views similar to FIGS. 7 and 8 but show still another embodiment of this invention. This embodiment is similar to the embodiment of FIGS. 7 and 8 in that the composite sheet 205 comprises an outer plastic film layer 2, an intermediate fibrous assembly layer 3 and an inner plastic film layer 5 all being similar to those layers of FIGS. 7 and 8. While the respective openings 9 substantially coincide with the corresponding openings 59 in the widths as well as the positions as measured and viewed in the direction X, this is not necessarily true for the positions as well as the widths of the bridge-like regions 10 and 60 as viewed and measured in the direction Y. The outer and inner film layers 2, 5 are provided along their edges 18, 68 with the rising regions 12, 62, respectively. These rising regions 12, 62 may comprise first and third rising regions 12A, 62A both extending upward, and second and fourth rising regions 12B, 62B extending downward. The rising regions 12A, 12B, 62A, 62B comprise those vertically extending up-or downward and those extending to lean inwardly of the openings 9 or 59. In the outer film layer 2, the openings 9A surrounded by the first rising regions 12A and the openings 9B. are formed alternately in the direction X. In the direction Y, the openings 9A surrounded by the first rising regions 12A are connected by the bridge-like regions 10 and the openings 9B surrounded by the second rising regions 12B also are connected by the bridge-like regions 10. In the inner film layer 5, the openings 59A surrounded by the third rising regions and the openings 59B surrounded by the fourth rising regions 62B are formed alternately inthe direction X. In the direction Y, the openings 59A are connected by the bridge-like regions 60 and the openings 593 also are connected by the bridge-like regions 60.

Though openings not illustrated, each pair of opposed edges 18, 18 with the openings 9 therebetween are formed along one of these edges with the first rising regions 12A and along the other edge with the second rising regions 12B. Similarly, each pair of opposed edges 68, 68 with the openings 59 are formed along one of these edges with the second rising regions 12B and along the other edge with the fourth rising regions 62B. With the panty liner 201 using the composite sheet 205 according to the embodiment shown by FIGS. 9 and 10, the first rising regions 12A of the outer plastic film layer 2 give the lower surface of the liner 201 a comfortable touch. The second rising regions 12B of the outer plastic film layer 2 extend inwardly of the fibrous assembly layer 3 to prevent the amount of menstrual discharge from sideways moving, particularly from sideways moving toward the openings 9. The fourth rising regions 62B of the inner plastic film layer 5 prevent the amount of menstrual discharge from sideways moving toward the openings 59. The component fibers 3A of the fibrous assembly layer 3 which are hydrophobic or preferably water repellent, can prevent the body fluids from flowing into the openings 59 without substantially reducing a total breathable area of the openings 59 so far as the component fibers 3A extend from the openings 59 toward the absorbent layer 202.

Of the first–fourth rising regions 12A, 12B, 62A, 62B, those extending so as to lean inwardly of openings 9 or 59 serve to intercept the amount of menstrual discharge absorbed by the absorbent layer 202 from the wearer's eyes when the liner 201 is looked from its lower side.

Figure 11:
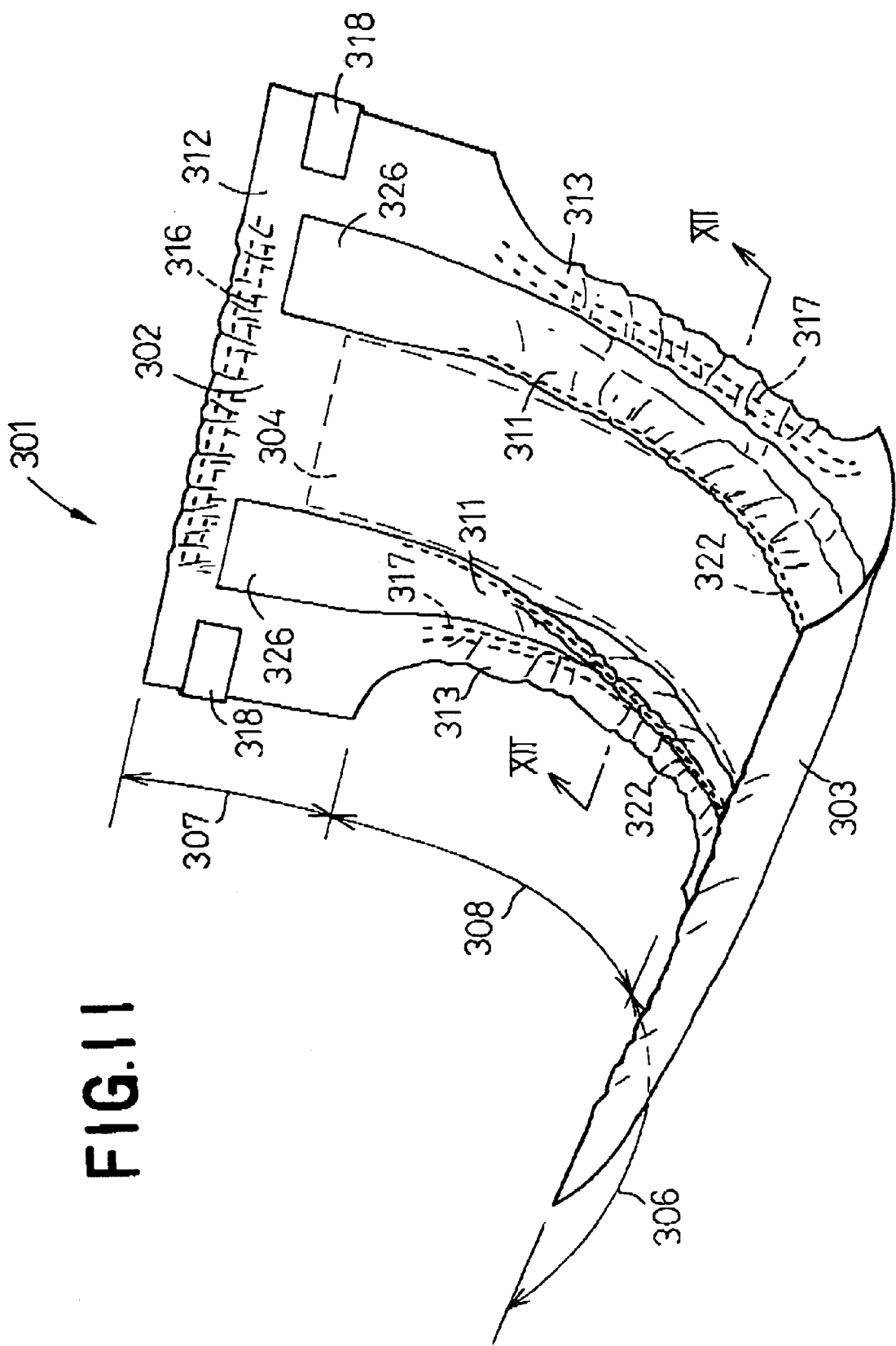
FIG. 11 is a perspective view of a disposable diaper.
Figure 12:
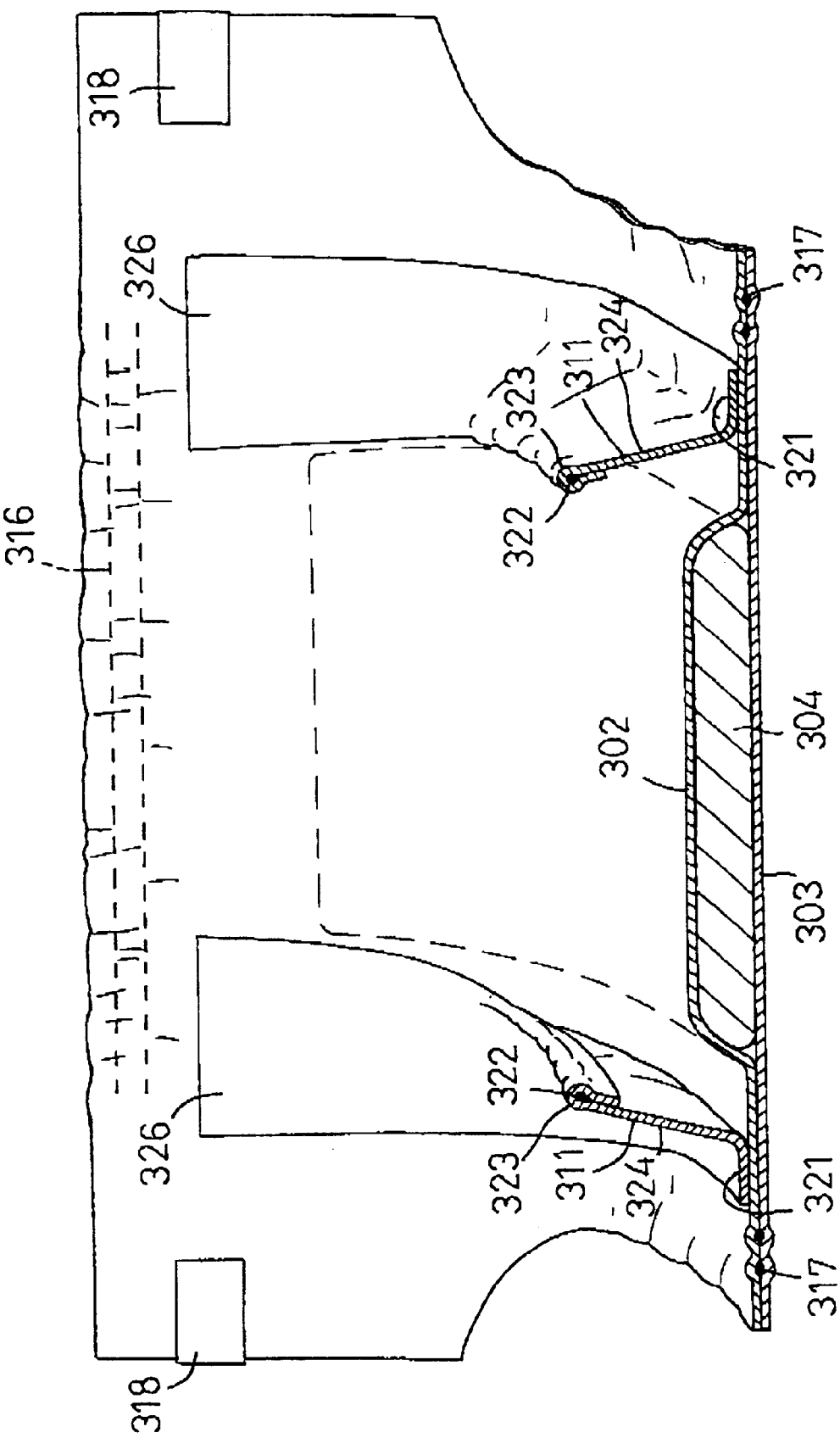
FIG. 12 is a sectional view taken along line XII—XII in FIG. 11.

FIG. 11 is a perspective view of a disposable diaper 301 and FIG. 12 is a sectional view taken along line XII—XII. The diaper 301 has inner and outer surfaces defined by a liquid-previous topsheet 302 and a liquid-impervious backsheet 303, respectively, and an absorbent core 304 is disposed between these two sheets 302, 303. The diaper 301 is longitudinally composed of a front waist region 306, a rear waist region 307 and a crotch region 308 extending between these two waist regions 306, 307. The diaper 301 is formed on its inner surface with a pair of leakage barriers 311 extending along transversely opposite side edges of the diaper 301 not only across the crotch region 308 but also across substantially entire ranges of the front and rear waist regions 306, 307. The diaper 301 is provided along a longitudinal end 312 of the rear trunk region 307 and transversely opposite side edges 313 of the crotch region 308 with an elastic member 316 associated with a waist-opening and elastic members 317 associated with leg openings, respectively. These elastic members 316, 317 are attached with a tension to the inner surfaces of the topsheet 302 and the backsheet 303. A pair of tape fasteners 318 are attached to transversely opposite side edges of the rear waist region 307.

The leakage barriers 311 are made of the composite sheet 205 illustrated in FIGS. 3–10, for example, FIGS. 9 and 10, each having a proximal edge 321 joined to the topsheet 302 by means of hot melt adhesive (not shown), a free edge 323 provided with an elastic member 322 longitudinally extending and secured under tension to said free edge 323 and an intermediate zone 324 extending between these two edges 321, 323. Longitudinally opposite ends 326 of each leakage barrier 311 are bonded over their entire width extending between the proximal edge 321 and the free edge 323 to the topsheet 302 by means of hot melt adhesive (not shown). With the leakage barriers 311 of such arrangement, contraction of the elastic member 322 causes the free edge 323 and the intermediate zone 324 to rise on the topsheet 302 as the diaper 301 is curved as shown in FIG. 11.

The leakage barriers 311 allow the outer plastic film layer 2 of the composite sheet 205 illustrated in FIG. 9 to be used so that the layer 2 may define the inner side or the outer side of the diaper 301. In any case, the leakage barriers 311 are liquid-resistant and can reliably prevent the body fluids discharged onto the diaper 301 from leaking sideways. In addition, the presence of the openings 9, 59 ensures a breathability of the leakage barriers 311 and the presence of the first and third rising regions 12A, 62A along the peripheral edges of these openings 9, 59 gives the wearer of the diaper 301 a soft touch. Furthermore, the first—fourth rising regions 12A, 12B, 62A, 62B function to prevent body fluids from flowing into the openings 9, 59 and to prevent the amount of body fluids having flowed into the openings 9, 59 from exuding back therefrom without substantially reducing the effective area of these openings 9, 59. In this manner, the liquid-resistance of the leakage barriers 311 is very effective. The hydrophobic fibrous assembly layer 3 has its fiber density appropriately adjusted so that a desired breathability may be ensured while body fluids may be prevented from both flowing into and exuding from the openings 9, 59. If desired, the outer plastic film layer 2, the inner plastic film layer 5 and/or the fibrous assembly layer 3 may be subjected to repellent finish to improve the liquid-resistance of the composite sheet 205.

The composite sheet 205 according to this invention satisfies all three requirements, i.e., touch, breathability and liquid-resistance and therefore can be used for various applications other than the panty liner and the diaper as illustrated. For example, the composite sheet 205 can be used as the stock material for disposable garments such as disposable gowns adapted to be used in medical sites or as component members of such disposable garments.

Figure 13:
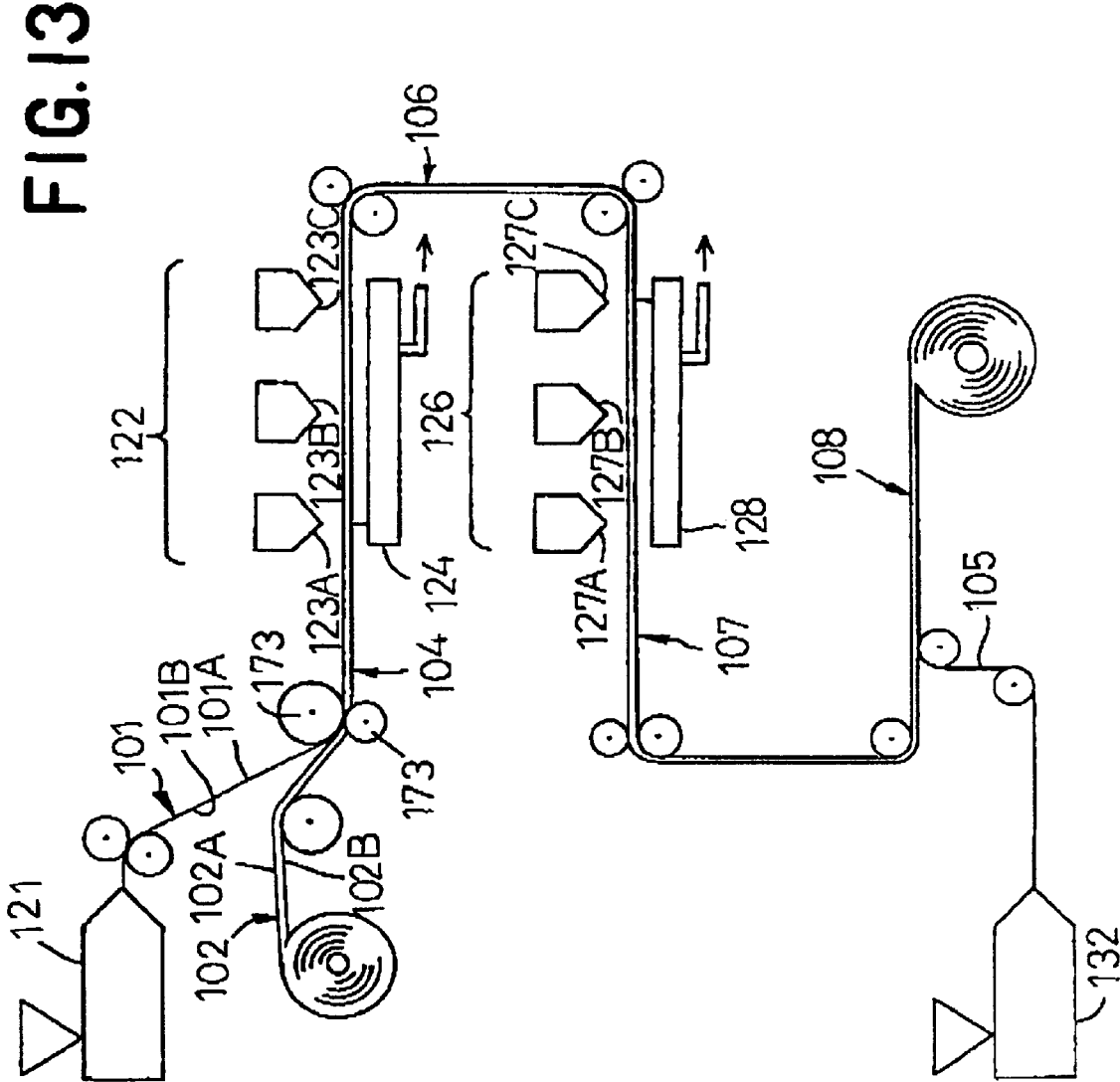
FIG. 13 is a diagram illustrating an embodiment of the process according to this invention for mating the composite sheet.

FIG. 13 is a diagram schematically illustrating an embodiment of the process according to this invention for making the composite sheet 205 of FIGS. 3 and 4. From the left hand as viewed in FIG. 13, a second web 102 comprising a hydrophobic fibrous assembly intended to form the intermediate fibrous assembly layer 3 is continuously fed. A first web 101 comprising a hydrophobic thermoplastic film web intended to form the outer plastic film layer 2 is fed from an extruder 121 so that the first web 101 in its thermally softened state may be placed upon the second web 102. These first and second webs 101, 102 placed upon each other are fed together between a pair of pressure rolls 173, 173 adapted to bond these two webs 101, 102 to each other and thereby to form a first composite web 104.

The first composite web 104 is then transferred to a first treating zone 122 in which the upper surface 101A of the first web 101 constituting the first composite web 104 is subjected to high pressure columnar water streams ejected from an array 123A of nozzles arranged at a predetermined pitch transversely of the first composite web 104. The first web 101 is broken through its locations at which the high pressure columnar water streams directly hit the first composite web 104. Consequently, the first web 101 is formed with a plurality of openings extending in a machine direction (i.e., a direction in which the first composite web 104 is fed) and arranged parallel one to another transversely of the first composite web 104. In this manner, a second composite web 106 is obtained. Under the effect of the columnar water streams, the component fibers may sometimes partially project downward from the lower surface 102B of the second web 102 so as to describe straight lines or circular arcs. It should be understood that the first treating zone 122 may be provided with, in addition to the array 123A of nozzles, second and third arrays 123B, 123C of nozzles adapted to eject the columnar water streams in order to from the plurality of openings. The nozzle arrays 123A, 123B, 123C are preferably arranged so that the individual nozzles in the respective arrays as viewed transversely of the first composite web 104 may occupy positions substantially aligned one with another and traces of the high pressure water streams may coincide one with another. The first treating zone 122 is provided as its lower part with a suction mechanism 124 adapted to such an excessive amount of water having treated the first composite web 104.

The second composite web 106 is then transferred to a second treating zone 126 provided with a plurality of nozzle arrays 127A, 127B, 127C each comprising a plurality of nozzles arranged transversely of the second composite web 106 and a suction mechanism 128. In the second treating zone 126, high pressure columnar water streams are ejected from the nozzle arrays against the lower surface 102B of the second web 102 making a part of the second composite web 106. The portions of the first web 101 having been broken through by the columnar water streams in the first treating zone 122 are now turned reversely by the columnar water streams, i.e., from the lower surface 101B toward the upper surface 101A of the first web 101 to form a third composite web 107. In this third composite web 107, the component fibers of the second web 102 partially project upward from this second web 102 under the effect of the columnar water streams so as to describe straight lines or circular arcs. It is not essential that the traces formed by the columnar water streams ejected from the nozzle arrays 127A, 127B, 127C should coincide with the traces formed by the columnar water streams ejected from the nozzle arrays 123A, 123B, 123C in the first treating zone 122. However, the steps of shooting through the first web 101 and reversely turning the portions of the first web 101 having been broken through by the columnar water streams in the first and second treating zones will be easily achieved if the traces formed by the nozzle arrays 123A~123C and the nozzle arrays 127A~127C coincide.

After the third composite web 107 has been subjected to a step of drying, a plurality of film strips 105 formed by a second extruder 132 are fed along the direction in which the third composite web 107 travels and bonded to the rear surface 102B of the second web 102 so that the film strips 105 extend parallel one to another. These film strips 105 are preferably joined immediately after they are formed by the second extruder 132, i.e., in their softened state, to the second web 102 under a pressure. In the third composite web 107, the film strips 105 are bonded to the rear surface 102B of the second web 102 so that the film strips 105 at least partially lie within the openings formed in the first web. A fourth composite web 108 obtained in this manner is taken up in the form of a roll and eventually cut in an appropriate size to use it as the composite sheet 205 of FIG. 3.

In the fourth composite web 108, the openings formed in the first web 101 are intended to define the openings 9 of the composite sheet 205 and the portions of the first web 101 shot through by the columnar water streams are intended to define the rising regions 12. The portions of the first web 101 having resisted against the columnar water streams are intended to define the bridge-like regions 10. The film strips 105 are intended to define the inner film layer 5 of the composite sheet 205.

Referring to FIG. 13, each of the nozzles in the arrays 123A~123C and 127A~127C preferably has a diameter of 50~150 μm, the nozzles in each array are arranged transversely of the first web 101 preferably at a pitch of 0.2–2 mm, a water pressure is preferably adjusted in a range of 30–200 kg/cm² and a suction pressure is preferably adjusted in a range of 200~1000 mm H₂O. In the first and second treating zones 122, 126, the web to be treated is placed on supporting means such as a mesh screen and conveyed in a desired direction. The first web 101 and the second web 102 as well as the second web 102 and the film strips 105 are fed at a room temperature and respectively bonded together by heat-sealed together between a pair of heated rolls or by use of adhesive agent such as hot melt adhesive agent.

The first web 101, the second web 102 and the film strips 105 may be treated, if desired, to make them hydrophilic at any step of the process for making the topsheet according to this invention. Formation of the openings by the high pressure columnar water streams is facilitated by using the first web 101 uniaxially stretched along the direction in which the first web 101 is fed. The first web 101 and the film strips 105 preferably have a thickness of 0.001~0.05 mm and the second web 102 preferably has a basis weight of 2–50 g/m².

In the process schematically illustrated by FIG. 13, the first treating zone 122 may be eliminated and the first composite web 104 may be subjected to the high pressure columnar water streams only in the second treating zone 126 to make the composite sheet 205. However, such process may result in the first web 101 having relatively narrow openings and relatively many bridge-like regions since the columnar water streams do not directly act upon the first web 101.

Figure 14:
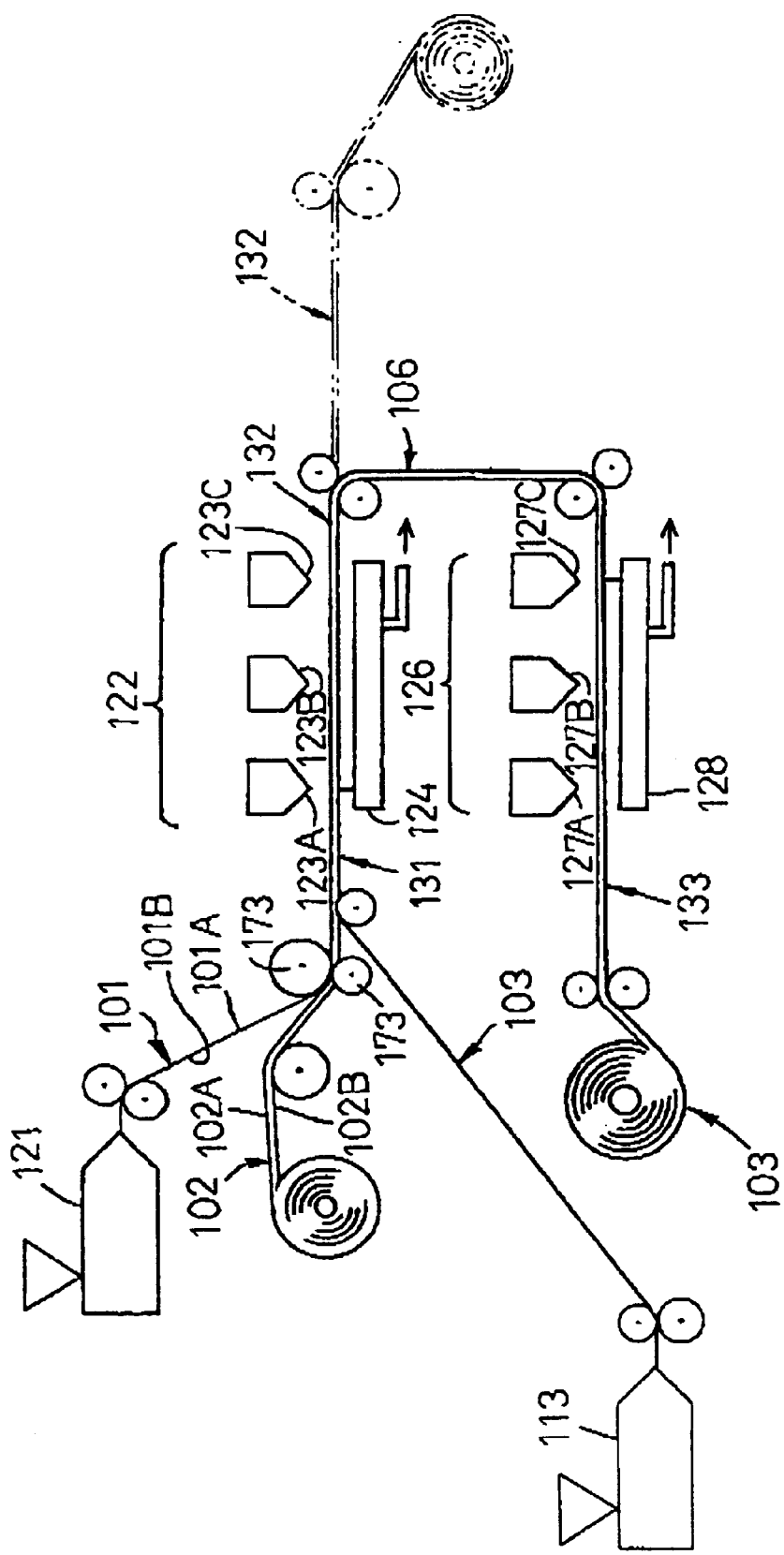
FIG. 14 is a diagram illustrating another embodiment of the process according to this invention for making the composite sheet.

FIG. 14 is a diagram similar to FIG. 13 but schematically illustrating another embodiment of the process suitable for making the composite sheet 205 of FIGS. 7, 8 as well as the composite sheet 205 of FIGS. 9, 10. According to this process, the first web 101 in the form of plastic film in softened state immediately after fed from the first extruder 121 is joined to the upper surface 102A of the second web 102 in the form of fibrous assembly, one hand, and the third web 103 in the form of plastic film in softened state immediately after fed from a third extruder 113 is bonded to the lower surface 102B of the second web 102, on the other hand. The third web 103 is destined to define the inner plastic film layer 5 of the composite sheet 205. In this manner, a fifth composite web 131 is obtained. The fifth composite web 131 has its first web 101 treated by the high pressure columnar water streams ejected from the nozzle arrays 123A, 123B, 123C in the first treating zone 122. As a result, a sixth composite web 132 is obtained, in which the first and web 101 and the third web 103 both made of plastic film are formed with a plurality of plane regions and a plurality of openings both extending in the machine direction. The sixth composite web 132 may be taken up in the form of a roll as indicated by imaginary lines. The sixth composite web 132 taken up in this manner has, in addition to the plane regions and the openings, the rising regions extending from the edges of the plane regions in the direction of the water streams and the bridge-like regions extending across the respective openings all formed in the first and third webs 101, 103. Such sixth composite web 132 is useful as the composite sheet 205 of FIGS. 7 and 8, in which the first web 101, the openings, the rising regions and the bridge-like regions formed in the first web 101 are intended to define the inner plastic film layer 5, the openings 59 and the rising regions 62 of the composite sheet 205, respectively. The third web 103, the openings, the rising regions and the bridge-like regions formed in the third web 103 are intended to define the outer plastic film layer 2, the openings 9, the rising regions 12 and the bridge-like regions 10 formed in the third web 103. The component fibers of the second web 102 may project up-or downward from the openings 59. The third web 103 preferably is made of film having a thickness of 0.001~0.05 mm.

It is also possible to convey the sixth composite web 132 to the second treating zone 126 instead of taking up in the manner as has been described above. In this case, the sixth composite web 132 has its third web 103 is subjected to the high pressure columnar water streams ejected from the nozzle arrays 127A, 127B, 127C in the second treating zone 126 to obtain a seventh composite web 133. A distance between each pair of adjacent nozzles in the respective nozzle arrays 127A, 127B, 127C each arranged transversely of the sixth composite web 132 is preferably dimensioned to be two fold or integral-fold larger than the corresponding distance in the first treating zone 122 and some of the nozzles in the second treating zone 126 are preferably positioned to substantially coincide with some of the nozzles in the first treating zone 122. By arranging the nozzles in the second treating zone 126, some of the openings in the sixth composite web 132 arranged transversely of this composite web 132 will be treated again in the second treating zone 126. In the vicinity of these retreated openings, the rising regions of the first and third webs 101, 103 are reversely turned by the columnar water streams to rise from the third web 103 toward the first web 101. At the same time, the component fibers of the second web 102 may project upward from the openings. In the openings not treated in the second treating zone 126, the rising regions remain to be oriented as in the sixth composite web 132. Of the seventh composite web 133, the first web 101 may be used as the outer plastic film layer 2 of the composite sheet 205 or alternatively the third web 103 may be used as the outer plastic film layer 2 of the composite sheet 205. on this step, The pitches at which the nozzles are arranged in the respective nozzle arrays 127A, 127D and 127C may be adjusted to convert the regularly alternate arrangements of the openings 9A, 913 and the openings 59A, 59B as illustrated in FIG. 9 to the other arrangements, for example, rather irregular arrangements, respectively.

It should be understood that the second treating zone 126 may include, in addition to the nozzle arrays 127A, 127B, 127C adapted to reverse the orientation of the rising regions, nozzle arrays adapted to form the third web 103 and/or the first web 101 with new openings, new rising regions extending along these openings and new bridge-like regions extending across these respective openings.

What is claimed is:

1. A composite plastic sheet comprising:

a first hydrophobic plastic film layer defining an upper surface of said composite plastic sheet;

a second hydrophobic plastic film layer defining a lower surface of said composite plastic sheet; and a hydrophobic thermoplastic synthetic fibrous layer disposed between and joined to the first and second hydrophobic plastic film layers, said first hydrophobic plastic film layer having an upper surface, a lower surface, a thickness of from about 0.001 to about 0.05 mm, a plurality of substantially flat portions having widths of from about 0.03 to about 1 mm and extending in parallel to one another in a first direction, and a plurality of intermittent apertures extending in said first direction between said substantially flat portions so as to form a plurality of aperture rows extending in parallel one to another in said first direction, pairs of said flat portions having said aperture rows therebetween being interconnected by a plurality of bridge portions that extend therebetween and across said aperture rows, said bridge portions extending across the respective aperture rows are formed intermittently in a second direction orthogonal to the first direction, providing two types of bridge portions, those which extend upward or downward from the upper surface of the flat portions to the upper surface of the respective adjacent flat portions so as to describe arcs and those which are flush with the flat portion, said intermittent apertures being defined by edges of said substantially flat portions which extend in said first direction and edges of said bridges portions which extend in said second direction, said substantially flat portions being formed at least along said edges thereof which extend in said first direction with a plurality of first substantially pointed tooth-shaped portions which extend upward from upper surfaces of said substantially flat portions, said second hydrophobic plastic film layer comprising a plurality of discrete elongate strip portions that extend parallel to one another in the first direction and arc spaced apart in said second direction, individual ones of said plurality of discrete elongate strip portions being aligned and configured to lie beneath at least a portion of one of each of the aperture rows of the first hydrophobic plastic film layer.

2. The composite plastic sheet according to claim 1, wherein said fibrous layer contains less than 5 wt. % hydrophilic fibers.

3. The composite plastic sheet according to claim 1, wherein said substantial flat portion of the first hydrophobic plastic film layer are farther formed along said edges thereof which extend in said first direction with a plurality of second substantially pointed tooth-shaped portions which extend downward from lower surfaces of said substantially flat portions.

4. The composite plastic sheet according to claim 3, wherein said second substantially pointed tooth-shaped portions extend into fiber interstices of said fibrous layer.

5. The composite plastic sheet according to claim 1, wherein said second substantially pointed tooth-shaped portions of the substantially flat portions extend so as to lean toward adjacent ones of the substantially flat portions.

6. The composite plastic sheet according to claim 1, wherein said fibrous layer comprises a nonwoven fabric.

* * * * *